United States Patent
Jacobs et al.

(10) Patent No.: US 7,473,259 B2
(45) Date of Patent: Jan. 6, 2009

(54) IMPLANT STABILIZING INSTRUMENT, KIT AND METHOD

(75) Inventors: Andrew M. Jacobs, Fort Wayne, IN (US); Carolyn K. Day, Maumee, OH (US); Rhonda B. Clarke, Winona Lake, IN (US); Herbert E. Schwartz, Ft. Wayne, IN (US); John W. Kemppainen, Richland, MI (US); Prasanna Malaviya, Ft Wayne, IN (US); Anthony D. Zannis, Ft Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 869 days.

(21) Appl. No.: 10/609,768

(22) Filed: Jun. 30, 2003

(65) Prior Publication Data

US 2004/0267270 A1 Dec. 30, 2004

(51) Int. Cl.
*A61B 17/04* (2006.01)
(52) U.S. Cl. .......................................... 606/148; 606/96
(58) Field of Classification Search .................... 606/1, 606/139, 144, 145, 146, 147, 148, 149, 150, 606/222, 223, 96
See application file for complete search history.

(56) References Cited

U.S. PATENT DOCUMENTS

| | | | |
|---|---|---|---|
| 3,895,444 A * | 7/1975 | Small ........................... | 433/75 |
| 4,119,092 A * | 10/1978 | Gil ............................... | 606/96 |
| 4,627,425 A * | 12/1986 | Reese ........................... | 606/87 |
| 4,873,976 A | 10/1989 | Schreiber | |
| 4,880,429 A | 11/1989 | Stone | |
| 4,969,889 A * | 11/1990 | Greig ........................... | 606/97 |
| 5,007,934 A | 4/1991 | Stone | |
| 5,030,219 A * | 7/1991 | Matsen et al. ................. | 606/53 |
| 5,053,043 A * | 10/1991 | Gottesman et al. ........... | 606/148 |
| 5,108,421 A | 4/1992 | Fowler | |
| 5,108,438 A | 4/1992 | Stone | |
| 5,129,882 A | 7/1992 | Weldon | |
| 5,290,310 A | 3/1994 | Makower | |
| 5,306,311 A | 4/1994 | Stone | |
| 5,308,352 A * | 5/1994 | Koutrouvelis ................ | 606/130 |
| 5,320,633 A | 6/1994 | Allen | |
| 5,320,639 A | 6/1994 | Rudnick | |
| 5,374,268 A | 12/1994 | Sander | |
| 5,462,549 A * | 10/1995 | Glock .......................... | 606/86 |
| 5,496,336 A * | 3/1996 | Cosgrove et al. ............. | 606/148 |
| 5,522,826 A * | 6/1996 | Daily ........................... | 606/159 |

(Continued)

OTHER PUBLICATIONS

O'Connor's Textbook of Arthroscopic Surgery, 2nd ed., 1992, Chapter 19.

*Primary Examiner*—Darwin P Erezo

(57) ABSTRACT

A surgical instrument stabilizes an implant as the implant is secured to native tissue at a damaged tissue site such as in an intra-articular space. The instrument has a proximal end portion, a distal end portion and an intermediate portion. The distal end portion has a template for guiding an attachment mechanism into the implant and the adjacent native tissue. The distal end portion can also have barbs to engage the implant to enhance stabilization of the implant. Several instruments can be provided in a surgical kit with different lengths and shapes of distal end portions. A surgical kit could also contain modular distal end portions of varying sizes and shapes. A surgical method utilizing the stabilizing instrument is also disclosed.

28 Claims, 11 Drawing Sheets

U.S. PATENT DOCUMENTS

| | | | |
|---|---|---|---|
| 5,569,252 A | 10/1996 | Justin | |
| 5,681,353 A | 10/1997 | Li | |
| 5,697,933 A * | 12/1997 | Gundlapalli et al. | 606/96 |
| 5,702,418 A | 12/1997 | Ravenscroft | |
| 5,702,462 A | 12/1997 | Oberlander | |
| H1706 H * | 1/1998 | Mason | 606/87 |
| 5,704,941 A * | 1/1998 | Jacober et al. | 606/88 |
| 5,735,903 A | 4/1998 | Li | |
| 5,769,856 A * | 6/1998 | Dong et al. | 606/96 |
| 5,873,906 A | 2/1999 | Lau | |
| 5,919,225 A | 7/1999 | Lau | |
| 5,951,587 A | 9/1999 | Qureshi | |
| 5,968,052 A | 10/1999 | Sullivan | |
| 5,980,524 A | 11/1999 | Justin | |
| 5,993,475 A | 11/1999 | Lin | |
| 6,015,429 A | 1/2000 | Lau | |
| 6,042,610 A | 3/2000 | Li | |
| 6,056,778 A | 5/2000 | Grafton | |
| 6,129,729 A * | 10/2000 | Snyder | 606/72 |
| 6,143,012 A * | 11/2000 | Gausepohl | 606/185 |
| 6,152,935 A | 11/2000 | Kammerer | |
| 6,156,044 A | 12/2000 | Kammerer | |
| 6,176,880 B1 | 1/2001 | Plouhar | |
| 6,193,723 B1 * | 2/2001 | Cripe et al. | 606/88 |
| 6,238,402 B1 | 5/2001 | Sullivan | |
| 6,293,961 B2 | 9/2001 | Schwartz | |
| 6,306,156 B1 | 10/2001 | Clark | |
| 6,306,159 B1 | 10/2001 | Schwartz | |
| 6,319,271 B1 | 11/2001 | Schwartz | |
| 6,347,940 B1 * | 2/2002 | Gordils Wallis | 433/72 |
| 6,350,274 B1 | 2/2002 | Li | |
| 6,355,041 B1 * | 3/2002 | Martin | 606/62 |
| 6,371,959 B1 * | 4/2002 | Trice | 606/97 |
| 6,391,051 B2 | 5/2002 | Sullivan | |
| 6,692,503 B2 * | 2/2004 | Foley et al. | 606/96 |
| 2001/0023352 A1 | 9/2001 | Gordon | |
| 2002/0045896 A1* | 4/2002 | Michelson | 606/61 |
| 2002/0091393 A1* | 7/2002 | Gundlapalli et al. | 606/88 |

* cited by examiner

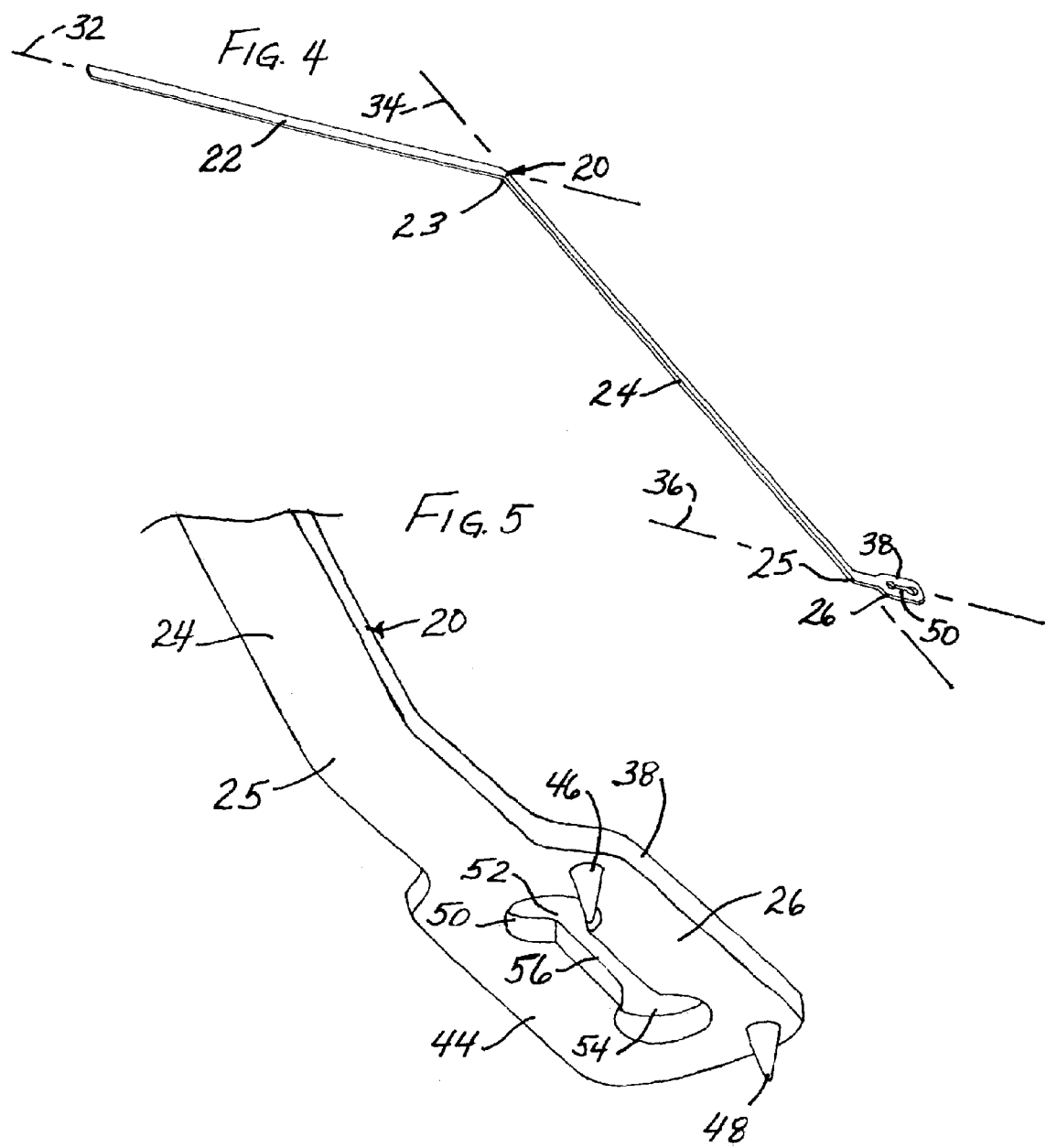

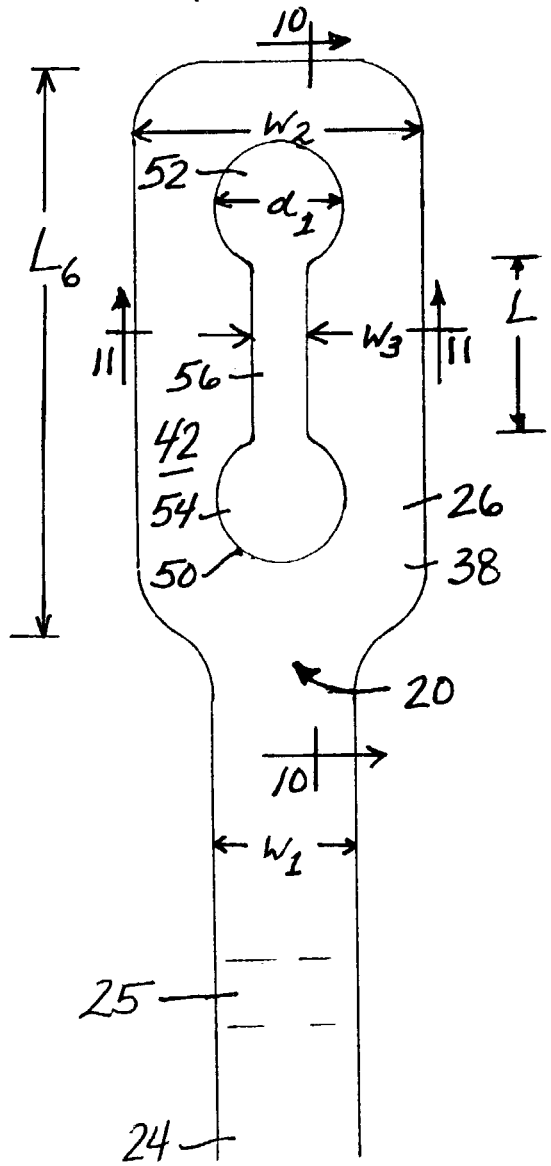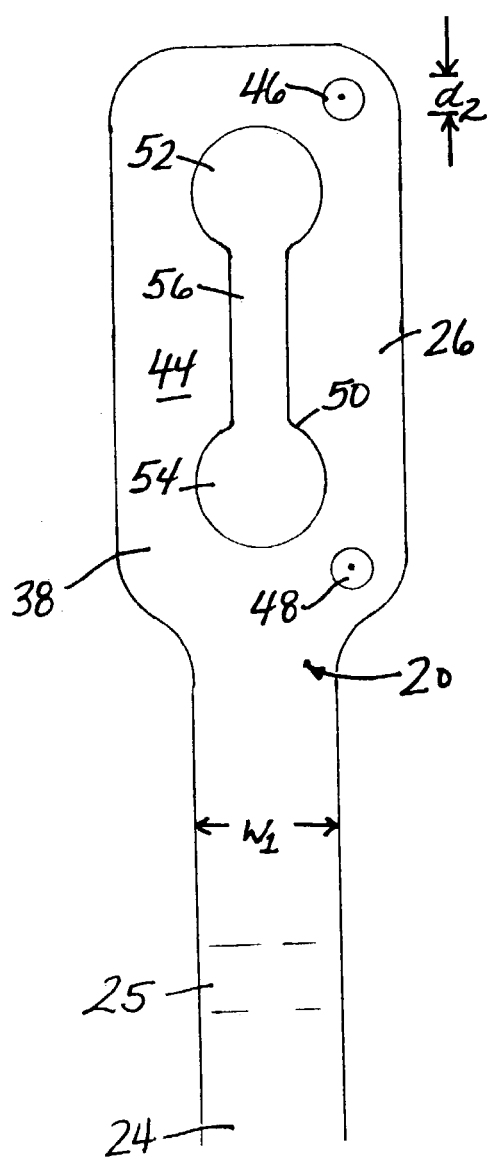

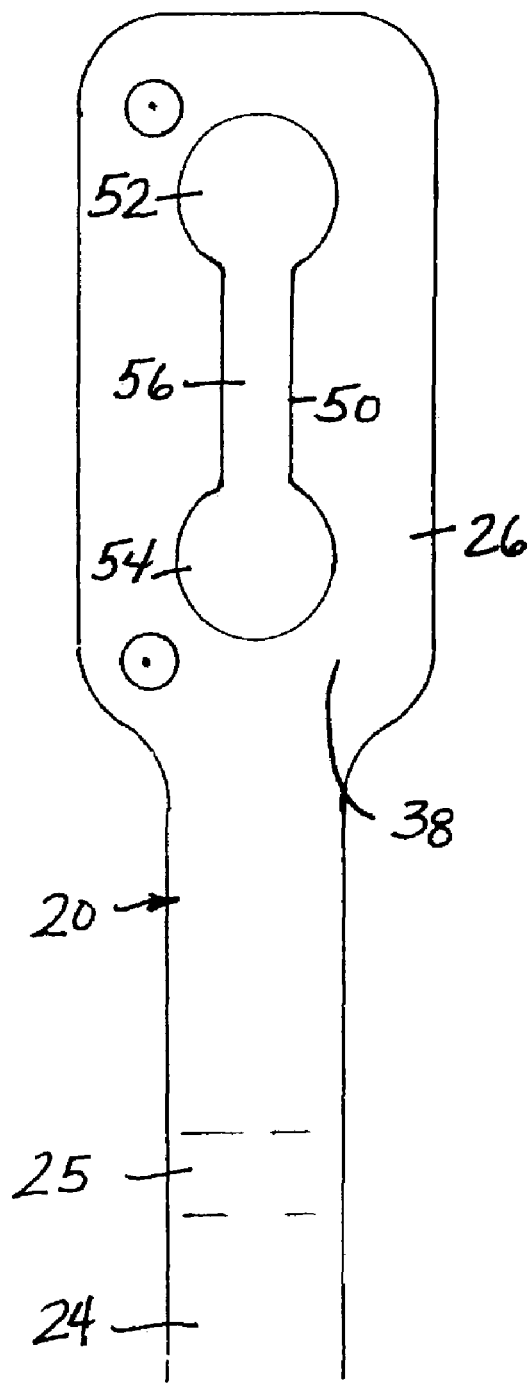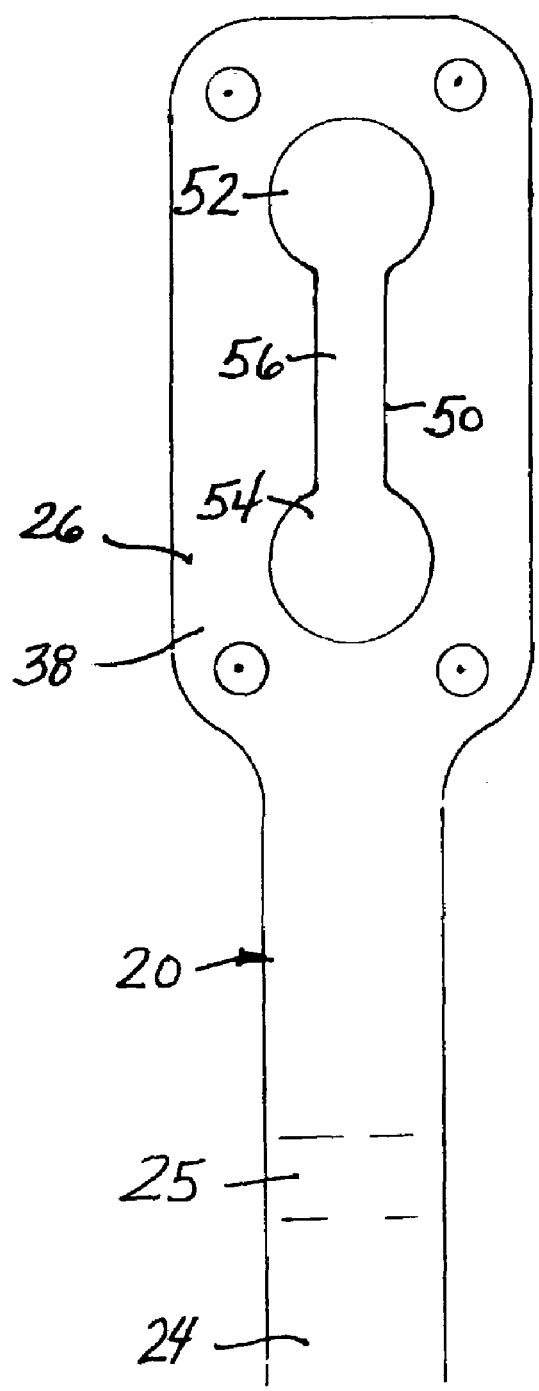

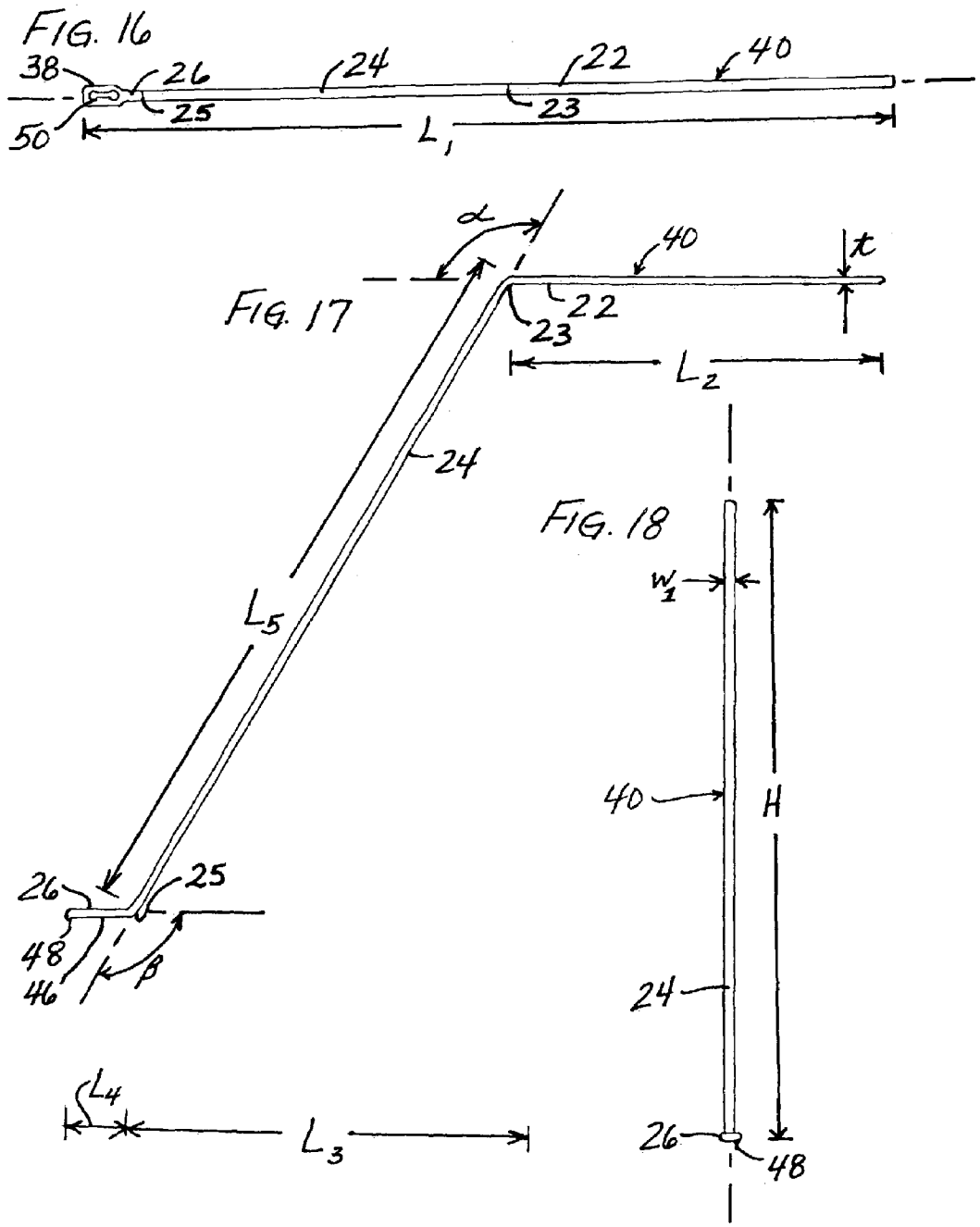

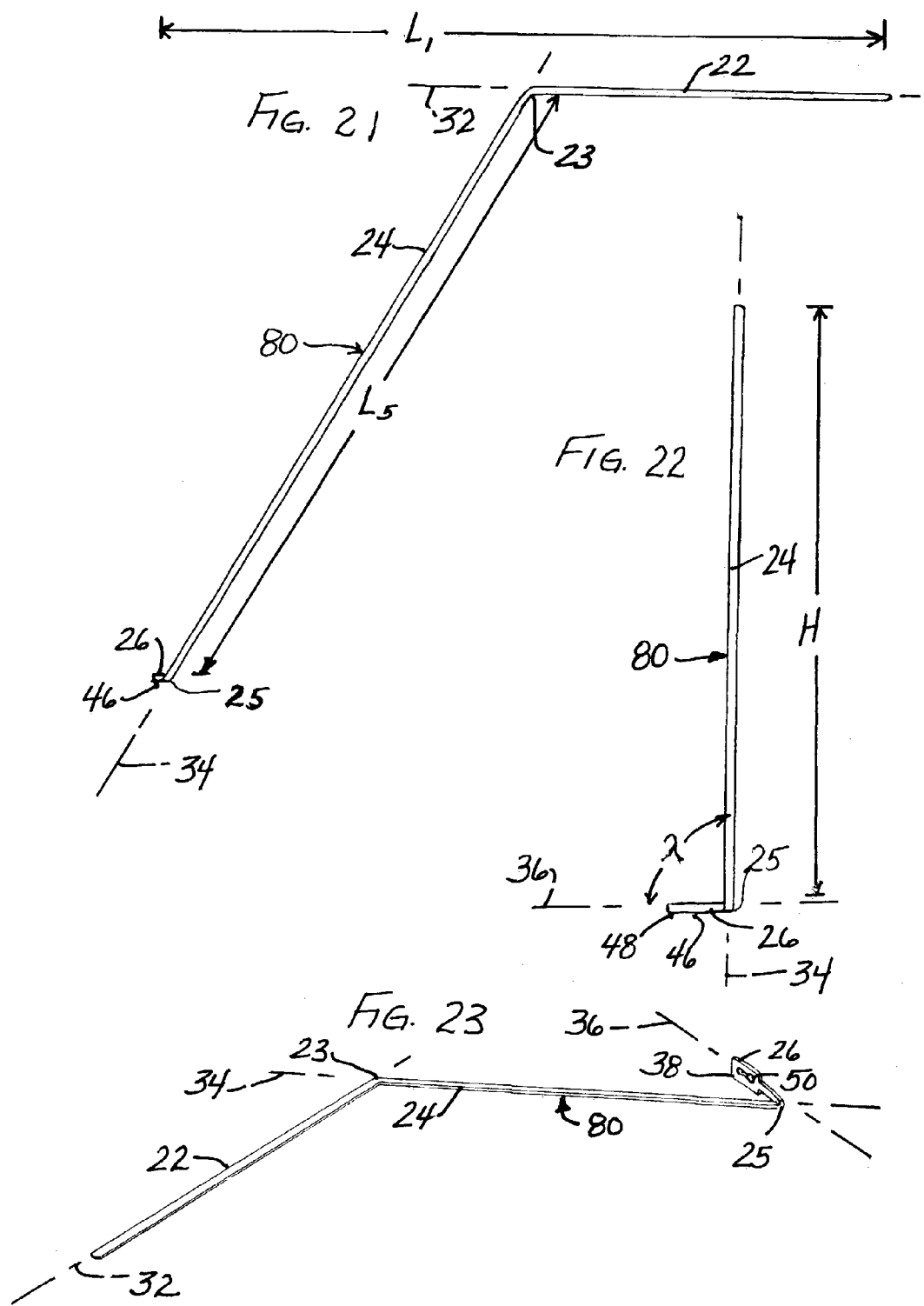

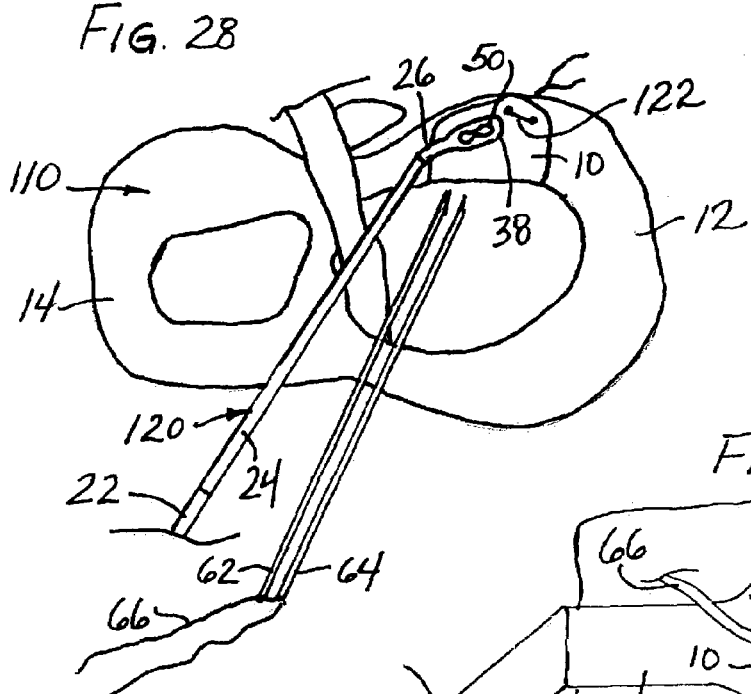
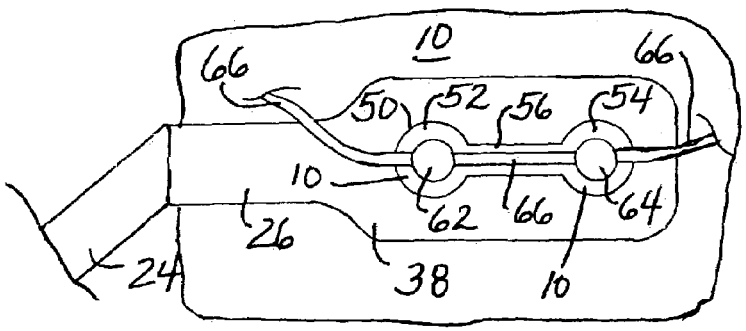
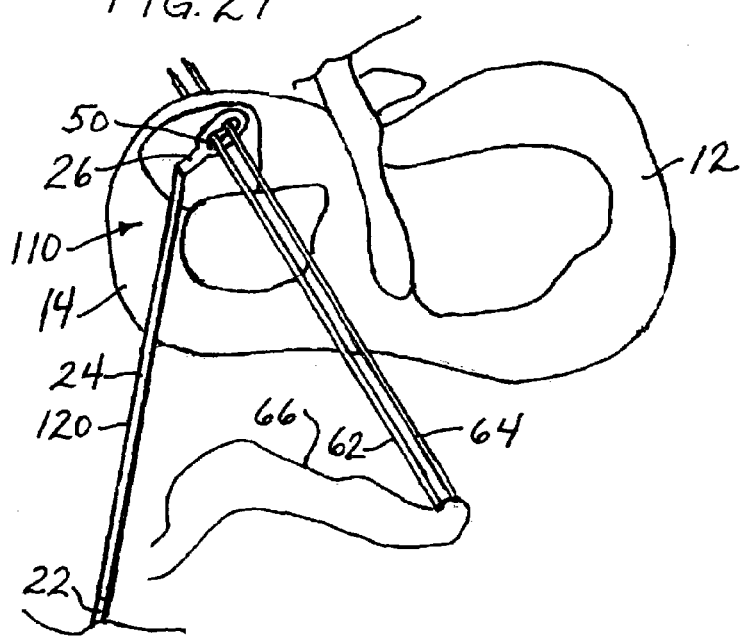

IMPLANT STABILIZING INSTRUMENT, KIT AND METHOD

FIELD OF THE INVENTION

The present invention relates to the repair and regeneration of soft tissue, and more particularly to a surgical instrument, kit and method for use in stabilizing an implant as the implant is secured to native tissue.

BACKGROUND OF THE INVENTION

Human joints have a type of cartilage known as intra-articular fibrocartilage. Intra-articular fibrocartilage can be present in the form of a discus articularis, that is, as a plate or ring of fibrocartilage in the joint capsule separating the joint surfaces (articular cartilage) of the bones of the joint. Such fibrocartilage is present, for example, in the temporomandibular joint, between vertebrae, and in the knee joint. In the knee joint, the intra-articular fibrocartilage comprises the meniscus, a crescent-shaped or semi-lunar-shaped disc of tissue that is located between the femoral condyles and the tibial plateau. The meniscus primarily functions as a shock absorber, absorbing the shock of compressive and shear forces in the knee. The meniscus also provides a substantially frictionless surface for articulation of the knee joint.

When cartilage tissue is no longer healthy, there can be debilitating pain in the joint. Cartilage health can be adversely affected by disease, aging, or trauma. The adverse effects of disease, aging and trauma can be in the form of a tear in the cartilage or in the form of a breakdown of the cartilage matrix.

In the knee, the meniscus is frequently damaged in twisting injuries. It is also damaged with repetitive impact over time. Meniscus degeneration can also occur by aging; as a person ages, the meniscus can become soft in places, so that even common motions like squatting can cause meniscal tears.

Common surgical procedures for treating meniscal damage include tear repairs and menisectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

Generally, an orthopaedic surgeon has several options in gaining access to damaged intra-articular fibrocartilage: a fully open arthrotomy, a mini-arthrotomy and the creation of several small portals for use in arthroscopy. In a fully open arthrotomy, a relatively large incision is made to expose the joint. In a mini-arthrotomy, a smaller incision is made to expose less of the joint; in knee surgery, the patella would not typically be subluxated in a mini-arthrotomy of the knee. In arthroscopy, small incisions are made at the affected joint to form portals for the insertion of instruments, including a small lens and lighting system (an arthroscope). The arthroscope is connected to a viewing device, such as a television camera to allow the surgeon to see the interior of the joint. Other instruments are inserted through other portals to perform a variety of tasks. For example, the surgical instrument may include an implement for manipulating native tissue (for example, tissue grasping, tissue cutting, bone abrading).

For faster healing, minimally invasive surgical procedures, such as arthroscopic procedures and mini-arthrotomies, are preferred. Typical surgical instruments used in arthroscopic procedures include rongeurs, such as the Kerrison rongeur, punch forceps, basket forceps, suction punches and cup curet, for example. Examples of arthroscopic instruments are described and illustrated in O'Cornor's Textbook of Arthroscopic Surgery, $2^{nd}$ ed., 1992, Chapter 19.

SUMMARY OF THE INVENTION

A variety of orthopaedic implants useful in approximating, repair or regeneration of fibrocartilage are disclosed in the following applications for U.S. patent Ser. No. 10/195,794 entitled "Meniscus Regeneration Device and Method" Ser. No. 10/195,719 entitled "Devices from Naturally Occurring Biologically Derived Materials" Ser. No. 10/195,347 entitled "Cartilage Repair Apparatus and Method" Ser. No. 10/195,344 entitled "Unitary Surgical Device and Method" Ser. No. 10/195,341 entitled "Hybrid Biologic/Synthetic Porous Extracellular Matrix Scaffolds" Ser. No. 10/195,606 entitled "Cartilage Repair and Regeneration Device and Method" Ser. No. 10/195,354 entitled "Porous Extracellular Matrix Scaffold and Method" Ser. No. 10/195,334 entitled "Cartilage Repair and Regeneration Scaffolds and Method" Ser. No. 10/195,633 entitled "Porous Delivery Scaffold and Method" each of which is assigned to the same assignee as the present application, each of which was filed on Jul. 15, 2002, and each of which is hereby incorporated by reference herein. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is incorporated by reference herein. Additional orthopaedic implants are disclosed in U.S. Pat. No. 6,176,880, entitled "Tissue Grant Construct for Replacement of Cartilaginous Structures" and U.S. patent application Ser. Nos. 09/767,345 and 09/767,346 of the same title, both filed on Jan. 23, 2001 and claiming priority to Pat. No. 6,176,880, which are incorporated by reference herein.

As used herein "orthopaedic iniplant" is intended to mean any device that is intended to be implanted at an intra-articular site for the approximation, repair or regeneration of fibrocartilage at the intra-articular site. "Orthopaedic implant" is intended to include all of the devices identified in the preceding paragraph, but is not limited to these particular devices unless expressly set forth in the claims.

The present invention addresses the need to attach such orthopaedic implants at an intra-articular site by providing a surgical instrument, kit and method for temporarily securing such an orthopaedic implant at an intra-articular surgical site of a joint, such as the knee.

In one aspect, the present invention provides a surgical instrument for stabilizing an implant as a surgeon introduces an attachment mechanism to secure the implant to native tissue at a damaged tissue site. The surgical instrument comprises a proximal end portion to be held by a surgeon, a distal end portion and an intermediate portion between the proximal end portion and distal end portion. The distal end portion defines an attachment template for guiding an attachment mechanism through the implant and into the native tissue at the damaged tissue site.

In another aspect, the present invention provides a surgical instrument for engaging and stabilizing an implant as suture is introduced to secure the implant to native tissue at a damaged tissue site. The instrument comprises a proximal end portion, a distal end portion and an intermediate portion. The proximal end portion is to be held by a surgeon, and has a central longitudinal axis. The distal end portion has a central longitudinal axis that is offset from the central longitudinal axis of the proximal end portion. The intermediate portion is between the proximal end portion and distal end portion. The intermediate portion has a central longitudinal axis that defines an angle of from about 30° to about 45° with the central longitudinal axis of the proximal end portion and an angle of from about 30° to about 45° with the central longitudinal axis of the distal end portion. The distal end portion has a top surface lying in a plane and a bottom surface lying in a plane and a pair of spaced guide holes extending from the top surface to the bottom surface. The spaced guide holes are sized and shaped to receive surgical needles. The spaced guide holes are connected by a slot extending from the top surface to the bottom surface. Together, the spaced guide holes and slot define a suturing guide for attaching the implant to native tissue at the damaged tissue site. The distal end portion also includes a plurality of spaced barbs extending outwardly from the bottom surface. The barbs are sized and shaped to extend through the implant and into the native tissue so that the distal end portion of the instrument can temporarily engage a portion of the implant as the implant is secured to the native tissue.

In another aspect, the present invention provides a surgical kit for stabilizing an implant as an attachment mechanism is introduced to secure the implant to native tissue at a damaged tissue site. The kit comprises a plurality of attachment templates for guiding an attachment mechanism through the implant and into the native tissue at the damaged tissue site. The attachment templates vary in at least one of the following characteristics: length and shape. Each attachment template is sized and shaped to be capable of being introduced arthroscopically to the damaged tissue site. The kit further includes at least one handle for guiding the templates to the damaged tissue site.

In another aspect, the present invention provides a method of attaching an implant to native tissue at a damaged tissue site. An implant is provided, along with an attachment mechanism for attaching the implant to the native tissue. A surgical instrument is also provided. The surgical instrument includes a proximal end portion to be held by a surgeon and a distal end portion. The distal end portion of the surgical instrument defines an attachment template for guiding an attachment mechanism through the implant and into the native tissue at the damaged tissue site. The implant is introduced to the damaged tissue site adjacent to native tissue. The distal end portion of the surgical instrument is introduced to the damaged tissue site. The distal end portion of the surgical instrument is placed against the implant to temporarily stabilize the position of the implant. The attachment mechanism is guided through the implant and into the native tissue with the attachment template while the distal end portion of the surgical instrument is against the implant.

Additional features of the present invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 4 is a perspective view of the surgical instrument of FIGS. 1-3;

FIG. 5 is an enlarged perspective view of the distal end portion of the surgical instrument of FIGS. 1-4;

FIG. 6 is an enlarged top plan view of the distal end portion of the surgical instrument of FIGS. 1-4;

FIG. 7 is an enlarged bottom plan view of the distal end portion of the surgical instrument of FIGS. 1-4;

FIG. 8 is an enlarged bottom plan view of an alternative distal end portion of a surgical instrument;

FIG. 9 is an enlarged bottom plan view of another alternative distal end portion of a surgical instrument;

FIG. 16 is a top plan view of a second embodiment of a surgical instrument illustrating the principles of the present invention;

FIG. 17 is an elevation or side view of the surgical instrument of FIG. 16;

FIG. 18 is an end view of the surgical instrument of FIGS. 16-17;

FIG. 21 is an elevation or side view of a fourth embodiment of a surgical instrument illustrating the principles of the present invention;

FIG. 22 is an end view of the surgical instrument of FIG. 21;

FIG. 23 is a perspective view of the surgical instrument of FIGS. 21-22;

FIG. 28 is a diagrammatic top plan view of a tibial plateau, showing a meniscal implant held in place on the medial meniscus by an alternative embodiment of a surgical instrument of the present invention, with a pair of double-armed suturing needles in the intra-articular space;

FIG. 29 is a diagrammatic top plan view of a tibial plateau, showing a meniscal implant held in place on the medial meniscus by an another alternative embodiment of a surgical instrument, with a pair of double armed suturing needles in the intra-articular space; and FIG. 30 is an enlarged top plan view of the distal end portion of the surgical instrument bearing against an orthopaedic implant, with surgical needles pushed through the guide holes of the instrument template and with a length of suture extending across the slot of the instrument template.

DETAILED DESCRIPTION

The instrument, kit and method of the present invention are useful in positioning an orthopaedic implant that has been delivered to an intra-articular site, to hold the implant in position while the orthopaedic implant is permanently attached to native soft tissue, and to providing a guide for placement of one or more attachment mechanisms for attaching the orthopaedic implant to the surrounding tissue.

The orthopaedic implant 10 (shown illustratively in FIGS. 27-29) may be, for example, a meniscal implant for use in the repair or regeneration of fibrocartilage after a partial meniscectomy. In the illustrated embodiments, the orthopaedic implant is implanted in the medial meniscus 12 (see FIGS. 27-29), although it should be understood that the instrument, kit and method of the present invention could be used on the lateral meniscus 14 (see FIGS. 27-29) as well. Although not illustrated, it is anticipated that the instrument, kit and method of the present invention can be used in conjunction with implanting orthopaedic devices in the intra-articular spaces of other joints as well; for example, in the temporomandibular joint or between vertebrae.

Figure 19:
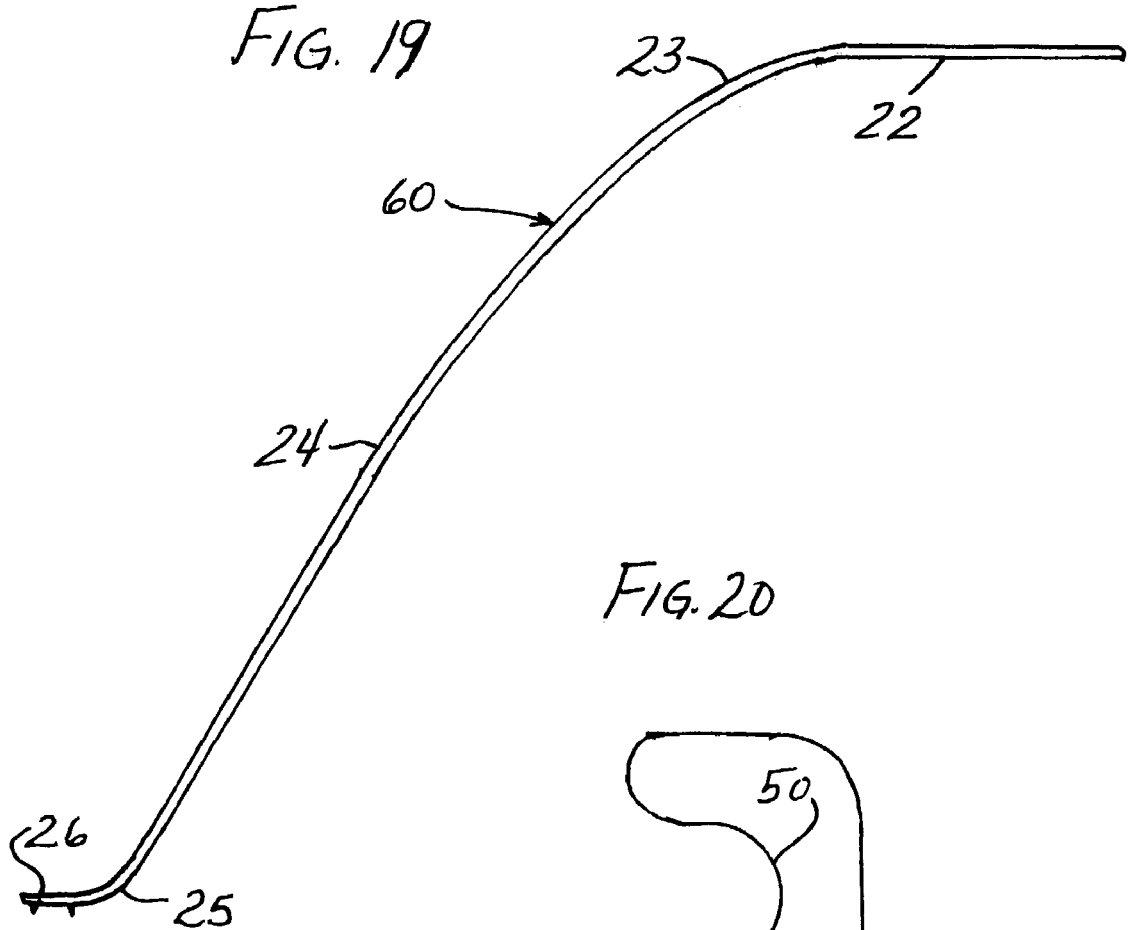
FIG. 19 is an elevation or side view of a third embodiment of a surgical instrument illustrating the principles of the present invention.

FIGS. 1-11 show a first embodiment of a surgical instrument for stabilizing an orthopaedic implant. The first embodiment of the instrument is designated 20 in the drawings. A second embodiment of a surgical instrument for stabilizing an orthopaedic implant is shown in FIGS. 16-18, and is generally designated 40. A third embodiment of the surgical instrument is shown in FIG. 19 and is generally designated 60. A fourth embodiment of the surgical instrument is shown in FIGS. 21-23 and is generally designated 80. In all of drawings of the surgical instruments, like reference numbers have otherwise been used for like parts.

Figure 27:
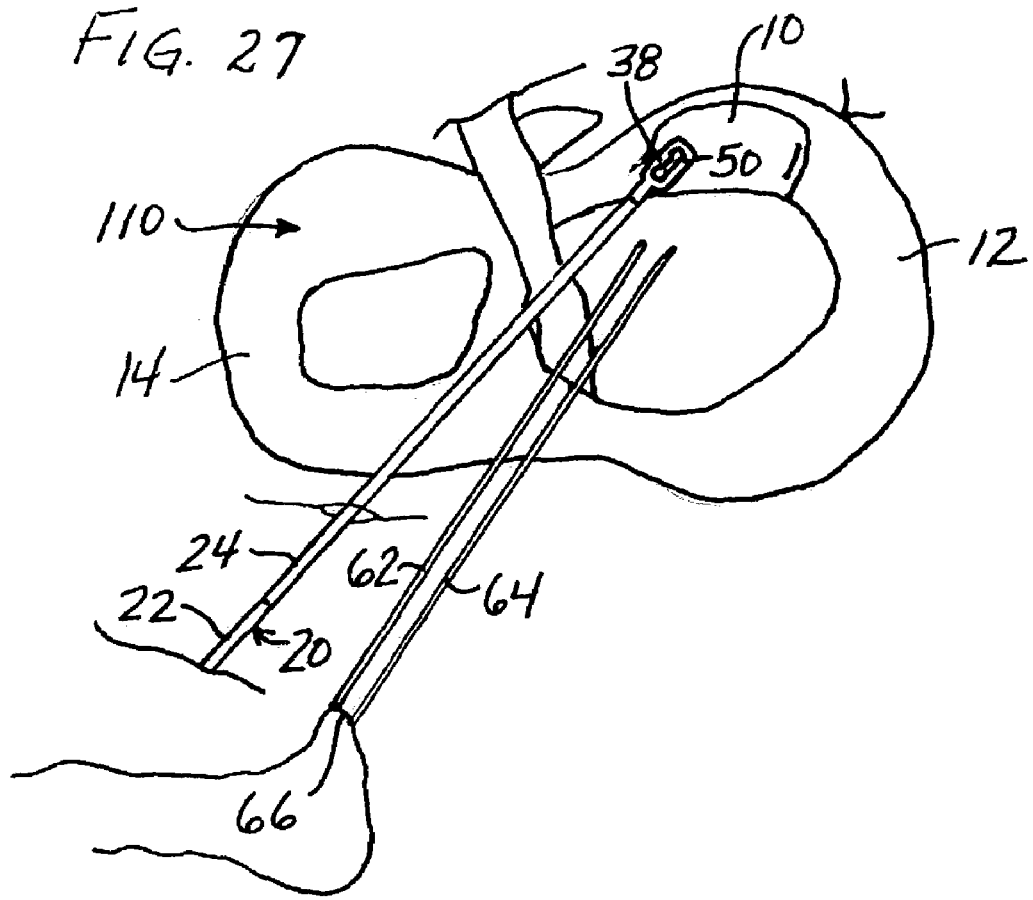
FIG. 27 is a diagrammatic top plan view of the tibial plateau, showing a meniscal implant held in place on the medial meniscus by the surgical instrument of FIGS. 1-7, with a pair of double armed suturing needles in the intra-articular space.

As shown in the drawings, all of the illustrated surgical instruments 20, 40, 60, 80 comprise a proximal end portion 22, an intermediate portion 24 and a distal end portion 26. The proximal end portion 22 is for the surgeon to grip, and the distal end portion 26 is for stabilizing the orthopaedic implant 10, as shown in FIGS. 27-29. In each embodiment, the intermediate portion 24 is connected to the proximal end portion 22 by a proximal transition portion 23. In each embodiment, the intermediate portion 24 is connected to the distal end portion 26 by a distal transition portion 25.

In the first and second illustrated embodiments 20, 40, the proximal transition portion 23 and distal transition portion 25 define angles between 0° and 180°. However, it should be understood that other shapes of transition portions may be used: for example, the transition portions 23, 25 can be curved, as shown in the embodiment designated 60 in FIG. 19. Likewise, although the illustrated proximal end portions 22, intermediate portions 24 and distal end portions 26 have substantially straight segments, they may also include or consist of curves.

Figure 1:
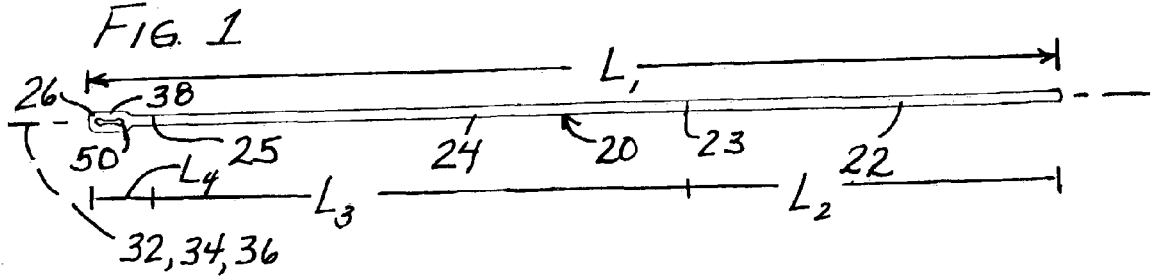
FIG. 1 is a top plan view of a first embodiment of a surgical instrument illustrating the principles of the present invention.
Figure 2:
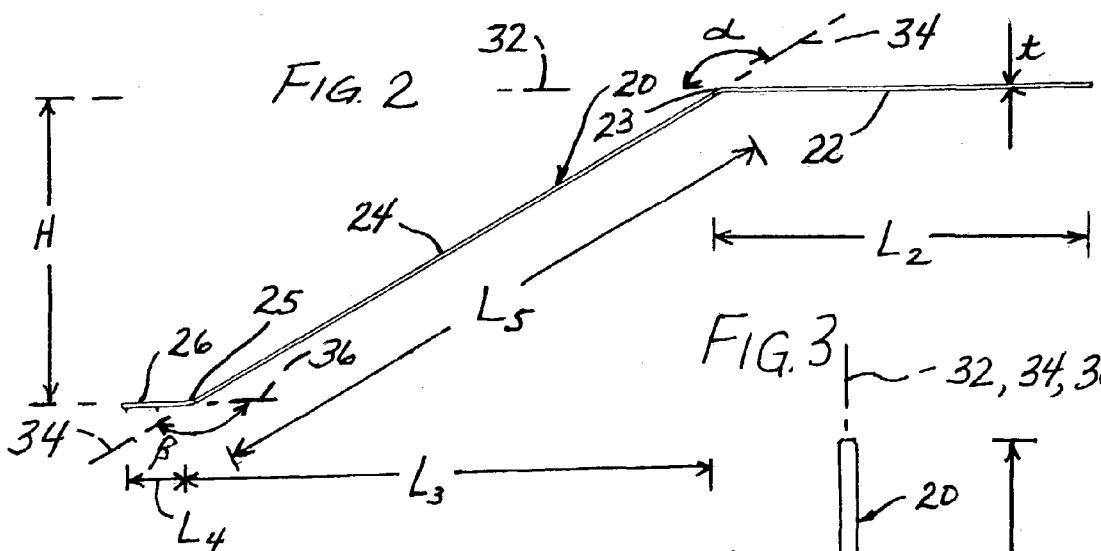
FIG. 2 is an elevation or side view of the surgical instrument of FIG. 1.
Figure 3:
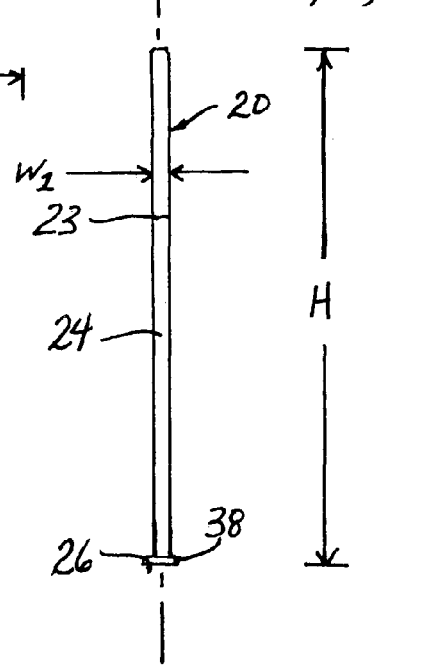
FIG. 3 is an end view of the surgical instrument of FIGS. 1-2.

As shown in FIGS. 1-3, the proximal end portion 22 has a central longitudinal axis 32, the distal end portion 26 has a central longitudinal axis 36 and the intermediate portion 24 has a central longitudinal axis 34. In the top plan view of FIG. 1 and the end elevation of FIG. 3, these three central longitudinal axes 32, 34 36 are aligned to be parallel. As shown in the side elevation of FIG. 2, the central longitudinal axis 32 of the proximal end portion 22 is offset from the central longitudinal axis 34 of the distal end portion 24. Also as shown in FIG. 2, the central longitudinal axis 32 of the proximal end portion 22 defines an angle α with the central longitudinal axis 34 of the intermediate portion 26 and the central longitudinal axis 36 of the distal end portion 26 defines an angle β with the central longitudinal axis 34 of the intermediate portion 24. The angles α and β may be greater than 0° and less than 180°; in the first illustrated embodiment, the angle α and the angle β are both 150°. In the surgical instrument 40 of FIGS. 16-18 the angle α and the angle β are both 120°. Thus, the central longitudinal axes 32, 36 of the two end portions 22, 26 of the instrument are generally parallel to each other in the first and second illustrated embodiments 20, 40. However, it should be understood that these values for the angles α and the β are given as examples only; the present invention is not limited to these or any other particular angle unless expressly set forth in the claims.

Although the central longitudinal axes 36 of the distal end portion 26 of the first three illustrated surgical instruments 20, 40, 60 are generally co-planar with the central longitudinal axes 32, 34 of the other portions 22, 24, the surgical instrument could have a different shape. For example, in the fourth illustrated surgical instrument 80 of FIGS. 21-23, the central longitudinal axis 36 of the distal end portion 26 is perpendicular rather than co-planar with the central longitudinal axes 32, 34 of the other portions 22, 24; this angle is shown at λ in FIG. 22. The value for the angle λ could vary from 90°. Providing such a variety of shapes for the surgical instruments of the present invention may be beneficial in providing the surgeon with greater flexibility in choosing the optimum shape of instrument for the particular procedure.

The surgical instruments 20, 40, 60, 80 have an overall length $L_1$ (shown in FIGS. 1, 16 and 21) and an overall height H (shown in FIGS. 2, 3, 18 and 22). In the first embodiment, $L_1$ is 7.817 inches and H is 2.51 inches. The length of the proximal end portion 22 of the first embodiment, shown at $L_2$ in FIGS. 1-2, is 2.98 inches; in the second embodiment, $L_2$ is 2.937 inches (see FIG. 17). The horizontal dimension of the intermediate portion 24 of the first embodiment, shown at $L_3$ in FIGS. 1-2, is 4.345 inches, and its overall length, shown at $L_5$ in FIG. 2, is 4.994 inches. In the second embodiment, $L_3$ is 2.979 inches (see FIG. 17), and at $L_5$ is 5.958 inches (see FIG. 17). The length of the distal end portion 26, shown at $L_4$ in FIGS. 1-2 and FIG. 17, is 0.491 inches in the first embodiment and 0.470 inches in the second embodiment. The surgical instrument 20 also has a thickness t: in the first embodiment, t is 0.02 inches throughout its length (see FIG. 2); in the second embodiment, t is 0.059 inches throughout its length (see FIG. 17). The width of the proximal end portion 22, intermediate portion 24 and a small part of the distal end portion 26, shown at $W_1$ in FIGS. 3, 6-7 and 18, is 0.079 inches in both the first and second embodiments (see FIGS. 3 and 18). It should be understood that these dimensions are provided by way of example only; the present invention is not limited to any particular dimension unless expressly set forth in the claims.

In the four illustrated instruments 20, 40, 60, 80, a substantial part of the distal end portion 26 has an enlarged surface area for stabilizing the orthopaedic implant 10. As best seen in FIG. 6, the enlarged part 38 of the distal end portion 26 has an increased width $W_2$ of almost double that of the remainder of the handle: in the illustrated embodiments, $W_2$ is 0.157 inches. The length of the enlarged part of the distal end portion 26, shown at $L_6$ in FIG. 6, is 0.315 inches. Generally, if the instrument is to be used in arthroscopic surgery, the width $W_2$ should be less than the inner diameter of a standard arthroscopic cannula, which is generally on the order of 5-10 mm. The length and width of the enlarged portion 38 should generally be such as to cover all or a portion of the surface area of the orthopaedic implant. As with other dimensions provided herein, these dimensions are provided as examples only; the invention is not limited to any particular dimension unless expressly set forth in the claims. In addition, although in the illustrated embodiments the enlarged parts 38 of the distal end portions have a generally rectangular shape with rounded corners in plan view, the invention is not limited to this particular shape. The shape of the distal end portion 26 may vary, for example, with the type of attachment mechanism to be used, and with the shape chosen for the template 50 discussed below.

The distal end portion 26 of each of the illustrated surgical instruments 20, 40, 60, 80 has a flat top surface 42 and a flat bottom surface 44. The bottom surface 44 carries a plurality of barbs 46, 48, described in more detail below.

In addition, the enlarged part 38 of the distal end portion 26 of each of the illustrated surgical instruments 20, 40, 60, 80 defines an attachment template 50 for guiding an attachment mechanism through the orthopaedic implant 10 and into the native soft tissue of the intra-articular space. As best seen in FIGS. 6-9, each attachment template 50 comprises a pair of spaced guide holes 52, 54 extending from the top surface 42 through the bottom surface 44 of the enlarged part 38 of the distal end portion 26 of the surgical instrument. Each guide hole 52, 54 has a diameter shown at $d_1$ in FIG. 6 of 0.06 inches. The centers of the guide holes 52, 54 are spaced a distance of 0.158 inches apart. The guide holes 52, 54 are connected together by a slot 56 having a width "$W_3$" of 0.02 inches. With these dimensions, the template 50 can be used to guide an attachment mechanism comprising double-armed suture needles, for example. An example of such an attachment mechanism is shown in FIGS. 26-29. Double armed suture needles are commercially available; for example, double armed trocar point STP-10 Needle pair with suture, is available from Ethicon, Inc. of Somerville, N.J. and double armed trocar point 13" Suture Needles with suture is available from Linvatec Corporation of Largo, Fla. As shown in FIGS. 26-29, such attachment mechanisms may include two suture needles 62, 64 with holes at their proximal ends through which is threaded a single common length of suture 66. It should be understood that these attachment mechanisms are provided as examples only; the present invention may be used with other attachment mechanisms and with other structures for delivering the attachment mechanisms to the site of the orthopaedic implant. Examples of various attachment mechanisms that may be used with orthopaedic implants are disclosed in U.S. patent application Ser. No. 10/195,344 entitled "Unitary Surgical Device and Method". The structures illustrated in FIGS. 6-9 may be used with each of the illustrated embodiments 20, 40, 60, 80 of the surgical instrument.

Figure 20:
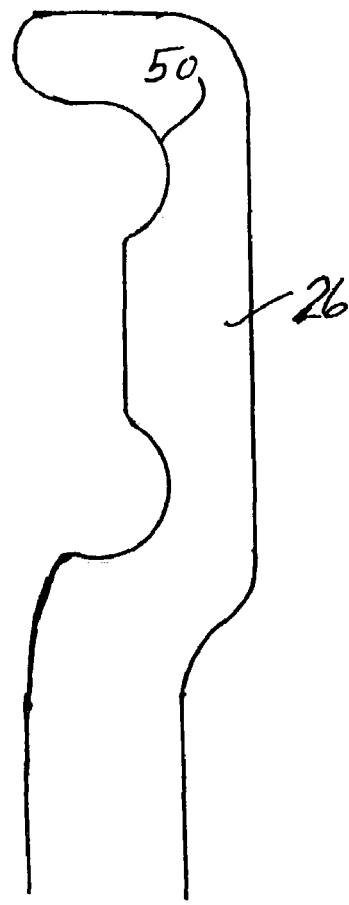
FIG. 20 is an enlarged top plan view of an alternative embodiment of the distal end portion of a surgical instrument.
Figure 26:
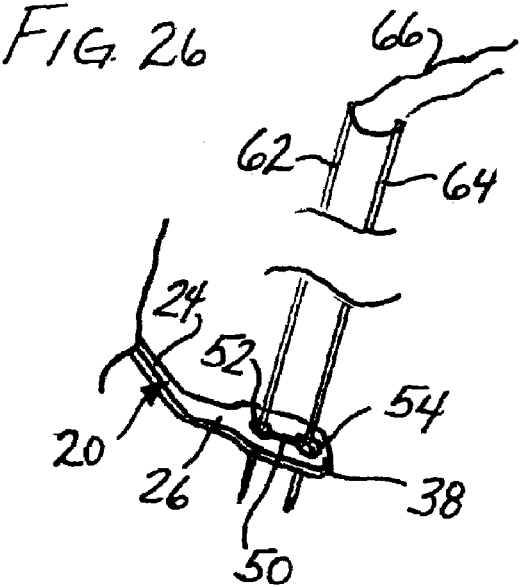
FIG. 26 is a partial perspective view of the distal end of an arthroscopic suturing guide with a pair of double-armed suturing needles extending through the suturing guide.

As shown in FIG. 26, each of the guide holes 52, 54 of the template 50 of the illustrated embodiments is sized and shaped to receive one of the needles 62, 64 of the double armed surgical needles; the spacing between the centers of the holes 52, 54 defines the length of the suture that will span the orthopaedic implant. The slot 56 is sized and shaped to be capable of receiving a length of suture 66 connected to the two suture needles 62, 64. It should be understood that the size and shape of the template 50 of the surgical instruments 20, 40, 60, 80 can be varied from that illustrated to accommodate the attachment mechanism and the instrument used to deliver and secure the attachment mechanism in place. An alternative design for the template 50 is shown in FIG. 20. These designs for the template can be used with each of the illustrated embodiments 20, 40, 60, 80 of the surgical instrument.

Figure 10:
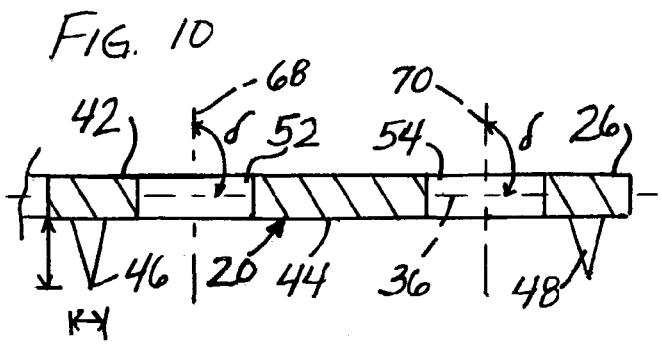
FIG. 10 is a longitudinal cross-section of the distal end portion of the surgical instrument of FIGS. 1-7, taken along line 10-10 of FIG. 6.
Figure 11:
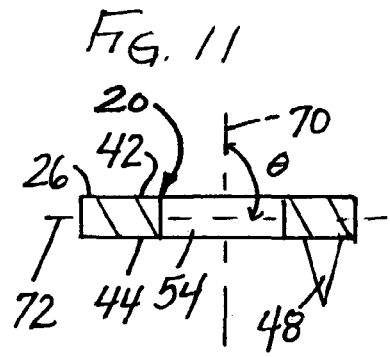
FIG. 11 is a transverse cross-section of the distal end portion of the surgical instrument of FIGS. 1-7, taken along line 11-11 of FIG. 6.
Figure 12:
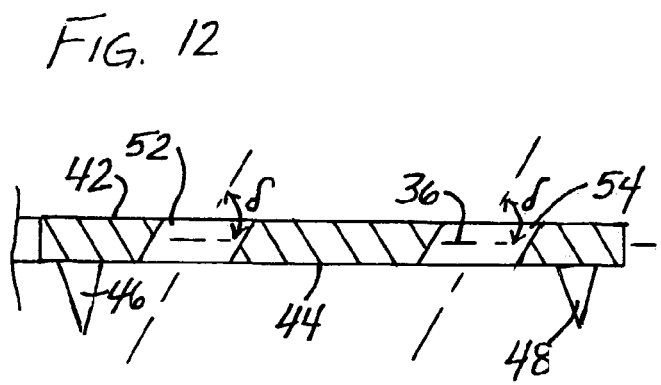
FIG. 12 is a longitudinal cross-section of an alternative distal end portion of a surgical instrument.
Figure 13:
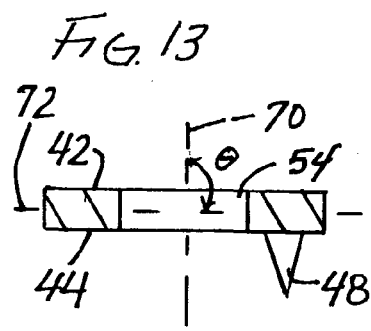
FIG. 13 is a transverse cross-section of the distal end portion of the surgical instrument of FIG. 12.
Figure 14:
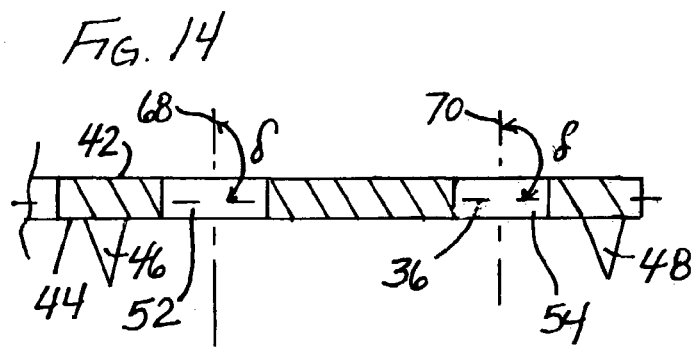
FIG. 14 is a longitudinal cross-section of another alternative distal end portion of a surgical instrument.
Figure 15:
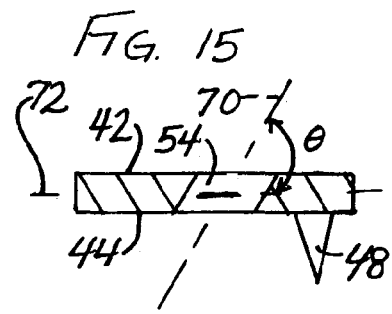
FIG. 15 is a transverse cross-section of the distal end portion of the surgical instrument of FIG. 14.

Each of the guide holes 52, 54 has a central longitudinal axis 68, 70. As shown in FIGS. 10-11, the axes 68, 70 may be perpendicular to the central longitudinal axis 36 of the distal end portion 26 and perpendicular to a plane 72 through the central longitudinal axis of the distal end portion 26. However, other orientations are also possible. For example, as shown in FIG. 12, the guide holes 52, 54 can be oriented to provide an angled entry path for the needles 62, 64. Thus, the longitudinal cross-sectional angle δ between the axes 68, 70 and the axis 36 can be 90° but can alternatively be another angle such as 60° for example; the axes 68, 70 could be oriented in a proximal-distal direction as shown in FIG. 12 or could alternatively be oriented in a distal-proximal direction. In addition, the transverse cross-sectional angle θ between the axes 68, 70 and the plane 72 of the axis 36 of the distal end portion can be 90° as shown in FIGS. 11 and 13, but can alternatively be another angle such as 60° for example; the axes 68, 70 could be oriented in a medial-lateral direction or lateral-medial direction. The axes 68, 70 of the guide holes 52, 54 could also be oriented with compound angles as well; that is, one or both the longitudinal angle δ and the transverse angle θ could be less than 90° so that the axes 68, 70 are oriented in both longitudinal and transverse cross-sections or in only one of these cross-sections. All of these configurations of guide holes can be used with each of the illustrated embodiments 20, 40, 60, 80 of the present invention.

To hold the orthopaedic implant in position while the implant is being attached to the surrounding native tissue, the bottom surface 44 of the distal end portion 26 of the instrument includes a plurality of barbs 46, 48. As best seen in FIGS. 5 and 7, the first illustrated instrument 20 has two barbs 46, 48 aligned along the one side of the distal end portion 26, that is, for example on the medial side. However, as shown in FIGS. 8-9, the barbs 46, 48 could be aligned along the lateral side, or along both the medial and lateral sides.

Each of the illustrated barbs 46, 48 has a generally conical shape, with a diameter of 0.021 inches shown at $d_2$ in FIG. 7. The sides of the conical barbs 46, 48 have a slope of 15° in the illustrated embodiment. The illustrated barbs 46, 48 extend outward from the bottom surface 44 of the distal end portion by a distance of 0.04 inches. It should be understood that these shapes and dimensions are provided as examples only; the invention is not limited to any particular shape or dimension for the barbs unless expressly set forth in the claims. Moreover, it should be understood that the present invention is not limited to the use of such barbs unless expressly set forth in the claims.

The sizes and shapes of the illustrated barbs 46, 48 allow for engaging the orthopaedic implant. With pressure, the illustrated barbs can pierce the orthopaedic implant to hold the implant in position. The illustrated barbs can also pierce native soft tissue to secure the position of the implant with respect to the native soft tissue.

The barbs 46, 48 described above can be used with each of the illustrated embodiments 20, 40, 60, 80 of the surgical instruments of the present invention.

Figure 24:
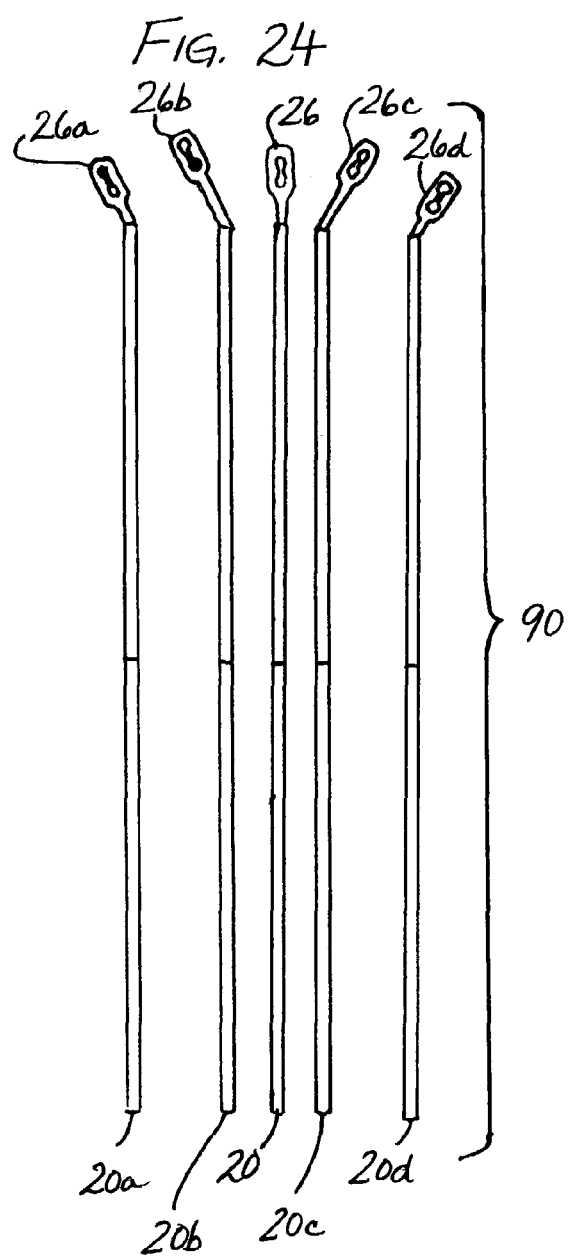
FIG. 24 is a top plan view of an embodiment of a surgical kit illustrating the principles of the present invention.
Figure 25:
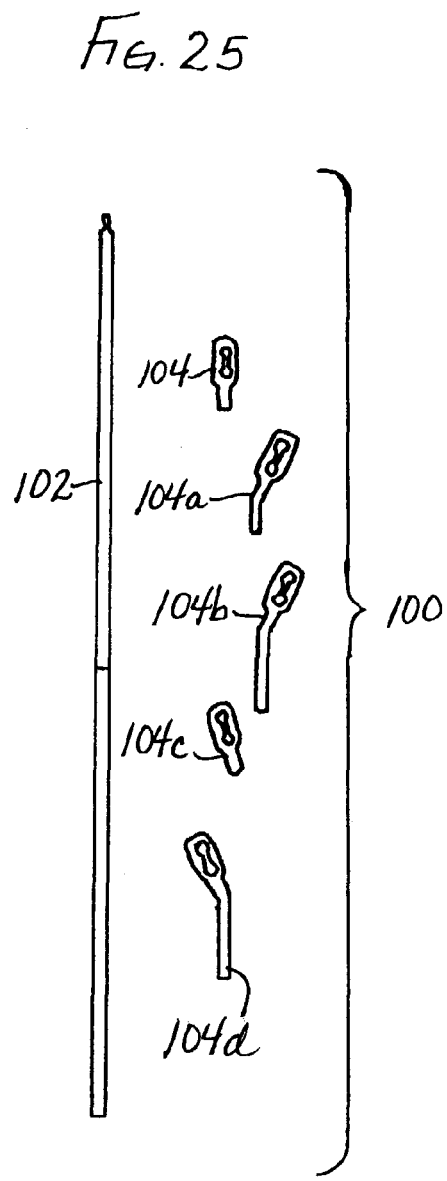
FIG. 25 is a top plan view of an alternative embodiment of a surgical kit illustrating the principles of the present invention.

The surgical instruments of the present invention can be supplied to the surgeon in the form of a kit. FIGS. 24 and 25 illustrate two possible kits that incorporate the teachings of the present invention. The surgical kit of the FIG. 24 embodiment is generally designated 90 and the surgical kit of the FIG. 25 embodiment is generally designated 100.

The surgical kit 90 of FIG. 24 contains a plurality of surgical instruments of the type described above. The kit 90 includes a surgical instrument 20 of the type shown in FIGS. 1-7 and others 20a, 20b, 20c, 20d having distal end portions 26a, 26b, 26c and 26d of different shapes and lengths. With these instruments 20, 20a, 20b, 20c, 20d, the surgeon has great flexibility in selecting which instrument to use or in using several of the instruments 20, 20a, 20b, 20c, 20d to secure or attach the orthopaedic implant in place. The different angular orientations of the distal end portions of these instruments in the kit allow for use on the right and left sides of the orthopaedic implant. The variation in shapes and lengths of the distal end portions allow for different instruments to be placed on different locations on the orthopaedic implant so that several attachment mechanisms easily can be placed through a single portal in arthroscopic surgery.

The surgical kit 100 of FIG. 25 provides the same flexibility to the surgeon as the kit 90 of FIG. 24, but does so by providing a modular design. The FIG. 25 kit 100 includes a single handle component 102 and a plurality of discrete distal end components 104, 104a, 104b, 104c and 104d. Each end component could have, for example, a different length and a different angular orientation. The handle component 102 and discrete distal end components 104, 104a, 104b, 104c and 104d can have mating mounting mechanisms for temporarily mounting an end component to the handle in a desired orientation; for example, mating keys and keyways could be provided to assure proper orientation of the modular components and mating tapers could be used to temporarily fix the components together. With such a modular surgical kit 100, the surgeon can select the distal end component or components most appropriate for the particular implant site for optimum location and orientation of the attachment mechanisms. The different angular orientations of the modular distal end portions in the kit allow for use on the right and left sides of the orthopaedic implant. The variation in shapes and lengths of the modular distal end portions allow for different modular distal end portions to be placed on different locations on the orthopaedic implant so that several attachment mechanisms easily can be placed through a single portal in arthroscopic surgery.

It should be understood that the kit 100 of FIG. 25 is an example of a modular kit; the handle and modular components could be divided in other locations, such as at a position nearer to the proximal end portion of the handle. Other variations are also possible; for example, a variety of template shapes could be provided in the kit to accommodate a variety of attachment mechanisms and a variety of instruments for delivering the attachment mechanisms.

Whether the surgical instruments are integral or modular, they may be made of any standard material used for surgical instruments. For example, an instrument or set of instruments could be made of surgical grade stainless steel. However, the invention is not limited to any particular material for the instrument or set of instruments unless expressly set forth in the claims.

The barbs 46, 48 could be made integral with the remainder of the distal end portion 26 or could be separately formed and then affixed to the distal end portion 26, such as by providing a cylindrical feature on the barb and a mating cylindrical hole in the distal end portion and inserting the cylindrical feature of the barb into the mating hole. The template 50 could be molded into the distal end portion 26 as it is formed or could be machined or cut into the distal end portion after the end portion 26 is formed.

The present invention also provides a method of attaching an orthopaedic implant 10 to native soft tissue in the intra-articular space of a joint. The method involves providing an orthopaedic implant and an attachment mechanism for attaching the orthopaedic implant to the native soft tissue in the intra-articular space of the joint. As discussed above, the attachment mechanism could comprise, for example suture, an anchor such as a barbed dart, a tack, a backstop, male and female locking members, and combinations of these devices. A surgical instrument of the type described above is also provided. A surgical kit with several surgical instruments, such as the kits 90, 100 could be used. FIG. 27 illustrates use of the first embodiment of the surgical instrument 20; FIGS. 28-29 illustrate use of a surgical instrument designated 120 that is similar to that shown in FIGS. 21-23, but with the distal end portion 26 at an opposite orientation.

The joint can be accessed through a full arthrotomy or through a mini-arthrotomy. Portals for arthroscopic surgery could alternatively be cut. The method of the present invention can be used with any of these surgical techniques, and the invention should not be considered to be limited to any particular technique unless expressly set forth in the claims.

The orthopaedic implant 10 is introduced into the intra-articular space adjacent native soft tissue. In FIGS. 27-29, the intra-articular space is generally designated 110. For example, the intra-articular space could be the space between the distal femur and proximal tibia in the knee joint, and the native soft tissue could be the meniscus 12, 14. FIGS. 27-29 illustrate use of the surgical instrument of the present invention with an orthopaedic implant to be secured or attached to the meniscus 12, 14; however, it should be understood that the surgical method of the present invention is not limited to meniscal surgery; the method can be applied to implantation of orthopaedic implants in other intra-articular spaces as well.

The orthopaedic implant 10 may be delivered or introduced to the intra-articular space 110 by any convenient method. If the surgery is performed arthroscopically, suitable instruments include an arthroscopic slide, as disclosed in U.S. patent application Ser. No. 10/610,287, entitled "SLIDE AND KIT FOR DELIVERING IMPLANTS", filed concurrently herewith by Thomas S. Camino, Anthony D. Zannis, John W. Kemppainen and Herbert E. Schwartz, which is incorporated by reference herein in its entirety. Another example of a suitable device for delivering or introducing an orthopaedic implant arthroscopically to an intra-articular site is disclosed in U.S. patent application Ser. No. 10/610,288, entitled "IMPLANT DELIVERY INSTRUMENT", filed concurrently herewith by Anthony D. Zannis, Thomas S. Camino, John W. Kemppainen, Herbert E. Schwartz and Danny E. McAdams, which is incorporated by reference herein in its entirety. Another example of a suitable device for delivering or introducing an orthopaedic implant to an intra-articular site arthroscopically is disclosed in U.S. Provisional Patent Application Ser. No. 60/483,804, entitled "INSTRUMENT FOR DELIVERY OF IMPLANT", filed concurrently herewith by Anthony D. Zannis, John W. Kemppainen, Andrew M. Jacobs, Carolyn K. Day, Rhonda B. Clarke, Herbert E. Schwartz, Prasanna Malaviya and Danny E. McAdams, which is incorporated by reference herein in its entirety. Although the present invention may be used in conjunction with any of these devices, it should be understood that use of the present invention is not limited to use with those devices.

The distal end portion 26 of the surgical instrument 20, 120 is introduced into the intra-articular space 110. This step may be accomplished before, during or after delivery of the orthopaedic implant to the space 110. If the surgery is performed arthroscopically, the distal end portion 26 of the instrument 20, 120 can be introduced through a cannula (not shown) in one of the arthroscopic portals. FIGS. 27-29 illustrate orientations of surgical instruments introduced through an anterior portal; however, it should be understood that the method of the present invention is not limited to use of anterior portals unless expressly set forth in the claims.

The surgical instrument 20, 120 can be used to engage the orthopaedic implant 10 and move it into its proper position, such as at the site of a menisectomy. To engage the orthopaedic implant 10, the bottom surface 44 of the distal end portion 26 of the instrument 20, 120 is placed against a surface of the orthopaedic implant so that the barbs 46, 48 engage the implant. For full engagement, the distal end portion 26 of the instrument 20, 120 may be pressed against the implant so that the barbs 46, 48 pierce the implant. However, it should be understood that frictional engagement between the barbs 46, 48 and the implant 10 may be sufficient.

Whether the surgical instrument 20, 120 or some other means is used to move the orthopaedic implant into the desired position adjacent native soft tissue, the surgical instrument of the present invention can then be used to temporarily secure this desired position of the orthopaedic implant as the implant is secured or attached to the native soft tissue.

As shown in FIGS. 27 and 28, with the position of the orthopaedic implant secured by the instrument 20, 120, the attachment mechanism can be introduced into the intra-articular space 110. FIGS. 27-29 illustrate introduction of double-armed trocar point needles 62, 64 with suture 66 extending between the proximal ends of the needles. If the surgery is performed arthroscopically, the attachment mechanism can be introduced through a cannula (not shown) in one of the portals.

If the surgery is performed arthroscopically, the surgeon can view the relative positions of the orthopaedic implant 10, the distal end portion 26 of the instrument 20, 120 and the distal ends of the needles 62, 64 through the arthroscope. Using the image provided by the arthroscope, the surgeon can guide the distal ends of the needles 62, 64 to the template 50, through the guide holes 52, 54 of the template 50, through the implant 10 and into and through adjacent native soft tissue, as shown in FIG. 29 while the bottom surface 44 of the distal end portion 26 of the instrument bears against the surface of the implant to secure the position of the implant 10.

The surgeon can then push the full lengths of the two needles 62, 64 through the guide holes, implant and soft tissue. As the surgeon does so, the suture 66 is pulled through the guide holes 52, 54 and slot 56 until a length of the suture is against the top surface of the implant, as shown in FIG. 30. After the needles have been pushed fully through the soft tissue, the ends of the suture are exposed at the edge of the native soft tissue. The surgeon can then tie the ends of the suture to secure or attach the implant to the soft tissue. A resulting suture attachment mechanism is shown at 122 in FIG. 28.

It should be understood that the above-described method might be varied to accommodate the particular type of attachment mechanism used and the method of exposing the joint during surgery.

Although the invention has been described with reference to the delivery of an orthopaedic implant to an intra-articular space, it will be appreciated that the invention has broader applications. For example, the instrument, kit and method of the present invention can also be used to stabilize an orthopaedic implant at a location outside of the intra-articular space of a joint site, such as in stabilizing an orthopaedic implant in the area of the rotator cuff of the shoulder joint site. The present invention can be used in stabilizing an orthopaedic implant at any damaged joint site.

It will also be appreciated that although the invention has been described with reference to an orthopaedic implant, the instrument, kit and method of the present invention can be used to stabilize implants for other purposes as well. The present invention could be used to stabilize any type of tissue scaffold, graft, or patch to any type of tissue, and the illustrated embodiments may be modified if desired to allow for such use. The present invention can thus be used to stabilize an implant at any damaged tissue site.

Unless otherwise expressly limited in the claims, "joint site" as used herein is intended to include the intra-articular space and other areas near the bones comprising a joint. "Damaged joint site", unless otherwise expressly limited in the claims, is intended to mean such a joint site that requires surgical repair, whether due to injury, degeneration or disease. "Damaged tissue site", unless otherwise expressly limited by the claims, is intended to mean a site within the body with damaged soft or bony tissue that requires repair, whether due to injury, degeneration or disease. And "implant", unless otherwise expressly limited by the claims, is intended to included orthopaedic implants as defined above and other devices intended to be implanted at a damaged tissue site for the approximation, repair or regeneration of native tissue at the damaged tissue site. An implant may comprise a tissue scaffold, patch or graft (including autografts, allografts and hetergrafts), for example. Moreover, an "implant" can include biocompatible synthetic materials, biocompatible natural materials or both such materials. In addition, "implant" and "orthopaedic implant" are intended to include such devices either alone or in combination with bioactive agents, biologically-derived agents, cells, a biological lubricant, a biocompatible synthetic or a biocompatible inorganic material, for example.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A surgical instrument for stabilizing an implant as a surgeon introduces an attachment mechanism to secure the implant to native tissue at the damaged tissue site comprising:
   a proximal end portion to be held by a surgeon, the proximal end portion having a longitudinal axis;
   a distal end portion having a longitudinal axis offset from the longitudinal axis of the proximal end portion;
   an intermediate portion between the proximal end portion and distal end portion, the intermediate portion having a longitudinal axis defining an obtuse angle with the longitudinal axis of the distal end portion;
   wherein the distal end portion defines an attachment template for guiding an attachment mechanism through the implant and into the native tissue of the damaged tissue site, including:
   a top surface lying in a plane and a bottom surface lying in a plane, a pair of spaced curved guide edges extending from the top surface to the bottom surface defining a pair of spaced guide holes sized and shaped to receive surgical needles, the distal end portion further including straight edges defining a slot between the spaced guide holes, the slot extending from the top surface to the bottom surface, the spaced guide holes and slot defining a suturing guide for attaching the implant to native tissue at the damaged tissue site; and a plurality of spaced barbs extending outwardly from the bottom surface of the distal end portion, the barbs being sized and shaped to extend through the implant and into the native tissue so that the distal end portion can temporarily engage a portion of the implant as the implant is secured to the native tissue.

2. The surgical instrument of claim 1 wherein the distal end portion of the surgical instrument is sized and shaped to fit in the intra-articular space of a joint.

3. The surgical instrument of claim 1 further comprising:
a proximal transition portion connecting the proximal end portion and the intermediate portion; and
a distal transition portion connecting the distal end portion and the intermediate portion.

4. The surgical instrument of claim 3 wherein the proximal transition portion and distal transition portion comprise curves.

5. The surgical instrument of claim 3 wherein the proximal transition portion and distal transition portion comprise angles between 0° and 180°.

6. The surgical instrument of claim 1 wherein each guide hole has a diameter and the slot has a width less that the diameters of the guide holes.

7. The surgical instrument of claim 6 wherein the guide holes are sized and shaped to receive and guide suture needles and the slot is sized and shaped to receive a length of suture.

8. The surgical instrument of claim 1 wherein:
the guide holes have central longitudinal axes;
the top surface and bottom surface of the distal end portion lie in substantially parallel planes; and
the central longitudinal axes of the guide holes are perpendicular to the planes of the top surface and bottom surface of the distal end portion.

9. The surgical instrument of claim 1 wherein:
the guide holes have central longitudinal axes;
the top surface and bottom surface of the distal end portion lie in substantially parallel planes; and
the central longitudinal axes of the guide holes define acute angles with the planes of the top surface and bottom surface of the distal end portion.

10. The surgical instrument of claim 1 wherein:
the longitudinal axis of the proximal end portion defines an angle greater than 0° and less than 180° with the longitudinal axis of the intermediate portion; and
the longitudinal axis of the distal end portion defines an angle greater than 0° and less than 180° with the longitudinal axis of the intermediate portion.

11. The surgical instrument of claim 1 wherein the longitudinal axes of the proximal end portion, intermediate portion and distal end portion are not co-linear and are not co-planar.

12. The surgical instrument of claim 11 wherein the longitudinal axes of the distal end portion and proximal end portion each defines an angle of from about 30° to about 45° with the longitudinal axis of the intermediate portion.

13. The surgical instrument of claim 1 wherein the proximal end portion, intermediate portion and distal end portion are integral.

14. The surgical instrument of claim 1 wherein the distal end portion is removable from the intermediate portion.

15. The surgical instrument of claim 1 wherein the instrument is sized and shaped so that the distal end portion can be introduced arthroscopically into an intra-articular space of a joint.

16. A surgical instrument for stabilizing an implant as a surgeon introduces an attachment mechanism to secure the implant to native tissue at the damaged tissue site comprising:
a proximal end portion to be held by a surgeon;
a distal end portion;
an intermediate portion between the proximal end portion and distal end portion;
wherein:
the distal end portion defines an attachment template for guiding an attachment mechanism through the implant and into the native tissue of the damaged tissue site, the distal end portion including a top surface and a bottom surface, a pair of spaced curved guide edges extending from the top surface to the bottom surface defining a pair of spaced guide holes sized and shaped to receive surgical needles, the spaced guide holes having diameters, the distal end portion further including straight edges defining a slot between the spaced guide holes, the slot extending from the top surface to the bottom surface, the spaced guide holes and slot defining a suturing guide for attaching the implant to native tissue at the damaged tissue site, the distal end portion further including a plurality of spaced barbs extending outwardly from the bottom surface, the barbs being sized and shaped to extend through the implant and into the native tissue so that the distal end portion can temporarily engage a portion of the implant as the implant is secured to the native tissue;
the proximal end portion has a central longitudinal axis;
the distal end portion has a central longitudinal axis;
the intermediate portion has a central longitudinal axis;
the central longitudinal axis of the proximal end portion is offset from the central longitudinal axis of the distal end portion; and
the central longitudinal axes of the proximal end portion, intermediate portion and distal end portion are co-linear in one view and are co-planar in another view.

17. The surgical instrument of claim 16 wherein the central longitudinal axes of the distal end portion and proximal end portion each defines an angle of from about 30° to about 45° with the central longitudinal axis of the intermediate portion.

18. A surgical instrument for engaging and stabilizing an implant as suture is introduced to secure the implant to native tissue at a damaged tissue site comprising:
a proximal end portion to be held by a surgeon, the proximal end portion having a central longitudinal axis;
a distal end portion having a central longitudinal axis offset from the central longitudinal axis of the proximal end portion;
an intermediate portion between the proximal end portion and distal end portion, the intermediate portion having a central longitudinal axis defining an angle of from about 30° to about 45° with the central longitudinal axis of the proximal end portion and an angle of from about 30° to about 45° with the central longitudinal axis of the distal end portion;
wherein the distal end portion has a top surface lying in a plane and a bottom surface lying in a plane and a pair of spaced guide holes extending from the top surface to the bottom surface, the spaced guide holes being sized and shaped to receive surgical needles, the spaced guide holes being connected by a slot extending from the top surface to the bottom surface, the spaced guide holes and slot defining a suturing guide for attaching the implant to native tissue at the damaged tissue site;

wherein the distal end portion includes a plurality of spaced barbs extending outwardly from the bottom surface, the barbs being sized and shaped to extend through the implant and into the native tissue so that the distal end portion can temporarily engage a portion of the implant as the implant is secured to the native tissue.

19. The surgical instrument of claim 18 wherein the instrument is sized and shaped so that the distal end portion can be introduced arthroscopically into an intra-articular space.

20. The surgical instrument of claim 18 wherein the central longitudinal axes of the proximal end portion, intermediate portion and distal end portion are co-linear in one view and are co-planar in another view.

21. The surgical instrument of claim 18 wherein the central longitudinal axes of the proximal end portion, intermediate portion and distal end portion are not co-linear and are not co-planar.

22. The surgical instrument of claim 18 wherein:
each guide hole has a central longitudinal axis;
the plane of the top surface of the distal end portion is parallel to the plane of the bottom surface of the distal end portion; and
the central longitudinal axes of the guide holes are perpendicular to the planes of the top surface and bottom surface of the distal end portion.

23. The surgical instrument of claim 18 wherein:
each guide hole has a central longitudinal axis;
the plane of the top surface of the distal end portion is parallel to the plane of the bottom surface of the distal end portion; and
the central longitudinal axes of the guide holes define acute angles with the planes of the top surface and bottom surface of the distal end portion.

24. The surgical instrument of claim 18 wherein the proximal end portion, intermediate portion and distal end portion are integral.

25. The surgical instrument of claim 18 wherein the distal end portion is removable from the intermediate portion.

26. A surgical kit for stabilizing an implant as an attachment mechanism is introduced to secure the implant to native tissue at a damaged tissue site comprising:
a plurality of attachment templates for guiding an attachment mechanism through the implant and into the native tissue at the damaged tissue site;
each attachment template including a top surface, a bottom surface parallel to the top surface, a pair of spaced curved edges defining a pair of spaced holes, straight edges connecting the holes and defining a slot between the spaced holes, and a plurality of barbs extending outward from the bottom surface;
wherein the attachment templates vary in at least one of the following characteristics: length and shape; and
wherein each attachment template is sized and shaped to be capable of being introduced arthroscopically to the damaged tissue site;
wherein the kit further includes at least one handle for guiding the templates to the damaged tissue site, the handle including a proximal portion having a central longitudinal axis and an intermediate portion having a central longitudinal axis, the central longitudinal axis of the intermediate portion defining an angle of from about 30° to 45° with the central longitudinal axis of the proximal portion.

27. The surgical kit of claim 26 wherein there are a plurality of handles and each attachment template is integral with one handle.

28. The surgical kit of claim 26 wherein each attachment template is removably mountable on the handle.

* * * * *